US009114266B2

(12) United States Patent
Ijiri et al.

(10) Patent No.: US 9,114,266 B2
(45) Date of Patent: Aug. 25, 2015

(54) COMPOSITION FOR COSMETICS HAVING UV SHIELDING EFFECT AND SEBUM SOLIDIFYING ABILITY, AND COSMETIC PREPARATIONS

(75) Inventors: Hirofumi Ijiri, Saitama (JP); Kazuo Sato, Saitama (JP); Masaharu Suzuki, Tokyo (JP); Yukio Hasegawa, Kasukabe (JP)

(73) Assignee: MIYOSHI KASEI, INC., Saitama-Shi (JP)

( * ) Notice: Subject to any disclaimer, the term of this patent is extended or adjusted under 35 U.S.C. 154(b) by 203 days.

(21) Appl. No.: 13/391,707

(22) PCT Filed: Jun. 29, 2010

(86) PCT No.: PCT/JP2010/004286
§ 371 (c)(1),
(2), (4) Date: Feb. 22, 2012

(87) PCT Pub. No.: WO2011/024364
PCT Pub. Date: Mar. 3, 2011

(65) Prior Publication Data
US 2012/0148511 A1   Jun. 14, 2012

(30) Foreign Application Priority Data
Aug. 31, 2009  (JP) ................................ 2009-200539

(51) Int. Cl.
| A61K 8/29 | (2006.01) |
| A61Q 1/00 | (2006.01) |
| A61Q 1/12 | (2006.01) |
| A61Q 19/00 | (2006.01) |
| A61Q 17/04 | (2006.01) |
| A61K 8/19 | (2006.01) |
| A61K 8/26 | (2006.01) |

(52) U.S. Cl.
CPC . *A61Q 17/04* (2013.01); *A61K 8/19* (2013.01); *A61K 8/26* (2013.01); *A61K 8/29* (2013.01); *A61Q 1/00* (2013.01); *A61Q 1/12* (2013.01); *A61Q 19/00* (2013.01)

(58) Field of Classification Search
USPC .................................................... 424/401, 59
See application file for complete search history.

(56) References Cited

U.S. PATENT DOCUMENTS

| 1,999,161 | A | * | 4/1935 | Walton ........................... 424/692 |
| 4,284,630 | A | * | 8/1981 | Yu et al. ....................... 514/179 |
| 5,362,482 | A | * | 11/1994 | Yoneyama et al. ............. 424/69 |
| 5,585,090 | A | * | 12/1996 | Yoshioka et al. ............... 424/59 |
| 5,961,961 | A | * | 10/1999 | Dobkowski et al. ........... 424/59 |
| 5,961,995 | A | | 10/1999 | Nishihama et al. |
| 6,030,627 | A | * | 2/2000 | Seo et al. ....................... 424/401 |
| 6,156,324 | A | | 12/2000 | Horino et al. |
| 6,759,052 | B1 | * | 7/2004 | Suzuki et al. ................. 424/401 |
| 7,357,918 | B2 | * | 4/2008 | Comte et al. .................... 424/59 |
| 2003/0031692 | A1 | | 2/2003 | Jager Lezer |
| 2007/0298000 | A1 | * | 12/2007 | Grune ............................ 424/59 |

FOREIGN PATENT DOCUMENTS

| JP | A-62-250074 | 10/1987 |
| JP | A-64-48881 | 2/1989 |
| JP | A-3-279323 | 12/1991 |
| JP | A-9-301828 | 11/1997 |
| JP | A-10-087420 | 4/1998 |
| JP | A-11-60220 | 3/1999 |
| JP | A-11-269303 | 10/1999 |
| JP | A-2002-293726 | 10/2002 |
| JP | A-2003-55150 | 2/2003 |
| JP | A-2004-315467 | 11/2004 |
| JP | A-2006-327961 | 12/2006 |

OTHER PUBLICATIONS

Sep. 7, 2010 International Search Report issued in International Application No. PCT/JP2010/004286 (with translation).
Nov. 26, 2012 Office Action issued in Chinese Patent Application No. 201080039592.8 (with concise explanation).
Sep. 9, 2013 Office Action issued in Chinese Patent Application No. 201080039592.8 (with concise explanation).
Jan. 15, 2014 Notice of Reasons for Rejection issued in Japanese Patent Application No. 2009-200539 (with translation and concise explanation).
Mar. 17, 2014 Office Action issued in Chinese Patent Application No. 201080039592.8 (with concise explanation).
Green, Joey, *Supermarket Spa*, Fair Winds Press, Gloucester, MA, 2005, p. 124.

* cited by examiner

*Primary Examiner* — Gina Justice
(74) *Attorney, Agent, or Firm* — Oliff PLC

(57) ABSTRACT

A composition for cosmetics is provided, which has a UV shielding effect and which can produce a cosmetic having good dispersibility, an excellent UV shielding effect and excellent use feeling, cosmetic effect, long-lasting cosmetic performance. The cosmetic obtained by using the same is provided. The composition for cosmetics includes (A) microparticulate titanium dioxide, (B) one kind or two or more kinds of magnesium hydroxide and calcium hydroxide. The composition for cosmetics preferably contains further (C) a clay mineral. The compounding weight ratio among (A): (B): (C) is preferably 20 to 60: 3 to 40: 0 to 77. In addition, the composition for cosmetics is preferably one in which a mixed powder of (A), (B) and (C) is lipophilically treated.

18 Claims, No Drawings ated again with the lapse of time, so that the SPF value not only decreases but also a cosmetic oil agent is denatured, and feeling is deteriorated. (Patent Document 1)

COMPOSITION FOR COSMETICS HAVING UV SHIELDING EFFECT AND SEBUM SOLIDIFYING ABILITY, AND COSMETIC PREPARATIONS

TECHNICAL FIELD

The present invention relates to a composition for cosmetics and cosmetics, which have a high UV shielding effect and sebum solidifying ability, the composition having good dispersability, a high UV shielding effect, long-lasting cosmetic effect, and excellent feeling of use

BACKGROUND TECHNOLOGY

It is known that the ultraviolet rays cause various adverse effects on the skin. The ultraviolet rays are classified into UV-A waves having 320 nm to 400 nm, UV-B waves of 290 nm to 320 nm and UV-C waves of not more than 290 nm according to the wavelengths. The UV-C waves are absorbed in the ozone layer, and almost all of them hardly reach the earth. When not less than a given amount of light of the UV-B waves reaching the earth is irradiated upon the skin, it forms an erythematous patch or a blister, so that the formation of melamine is promoted. Further, it is considered that the UV-A waves actually darken the skins, although they are less likely to cause the erythematous patch, as compared with the UV-B waves. Further, the UV-A waves have high permeability to the skins, promote the formation of crosslinking of collagen as a protein in the skins, lower the elasticity and water sustainability of collagen, promote the formation of wrinkles, and cause stains, freckles and skin aging. In addition, since the UV-A waves increase lipid peroxides of skin tissues, it is known that they cause skin cancers.

In order to protect the skins from damages with such ultraviolet rays, cosmetics containing various kinds of ultraviolet shielding agents have been heretofore developed and commercially available. As the various kinds of the ultraviolet shielding agents, there are organic ultraviolet absorbing agents such as benzophenones, aminobenzoic acids, cinnamic acid esters, benzotriazoles, salicylic acids and the like, and inorganic pigments such as titanium dioxide, zinc oxide, zirconia oxide, and iron oxides and the like.

Among them, the inorganic pigments having the ultraviolet shielding effect to be mixed into cosmetics, for example, titanium dioxide, are set to particle diameters in the Rayleigh scattering range, which is smaller than the wavelengths of the visible light. As the set powder particles are more dispersed in a state nearer to primary particle diameters, the ultraviolet ray scattering can be exhibited to the maximum. However, the smaller the primary particle diameters of the powder are, the greater is the specific surface area, so that contact points among the particles increase therefore the powder is more likely to be flocculated, and consequently the dispersability is deteriorated. Many techniques have been proposed as measures to avoid such flocculation as much as possible and prevent re-flocculation even with the lapse of time.

A suntan composition in which microparticulate titanium dioxide and microparticulate zinc oxide are mixed is proposed, for example, but a high SPF value is not obtained unless it is mixed at a high concentration (13 wt % or more). Further, high-concentration mixing is unfavorable in that it increases a hiding power and retains whiteness in a cosmetic film, and the particles are flocculated again with the lapse of time, so that the SPF value not only decreases but also a cosmetic oil agent is denatured, and feeling is deteriorated. (Patent Document 1)

Furthermore, cosmetics containing microparticulate titanium dioxide treated with silicone, microp articulate zinc oxide treated with silicone and a clay mineral treated with silicone are proposed. This can offer cosmetics having high stability free from change with the lapse of time, which have good dispersability and a high UV shielding effect, suppress optical activity and catalytic activity of an ultraviolet protecting material. Furthermore, regarding the lasting cosmetic quality, excess secretion of sebum causes make-up deterioration such as <unevenness>, <oily sheen>, <creasing>, <skin dullness>, <disappearance> and the like owing to change in a cosmetic film applied onto a skin with lapse of time, and further causes the production of a peroxide with oxygen in the atmosphere. When such stimulants enter the skin, they cause inflammation or abnormal cuticle, or results in spots or freckles like optically deteriorated fat and oil. Therefore, the cause of the above peroxide is prevented by blending zinc oxide, adsorbing and solidifying as an effective treatment of the skin under consideration of skin safety. However, safety of zinc oxide has been recently questioned, and some limitation is posed on uses thereof. (Patent Document 2)

As to the lasting cosmetic quality, a powder having a layer of hydroxy apatite and a layer of zinc oxide layer and a powder in which sericite particles are coated with amorphous calcium phosphate are proposed to provide cosmetics having excellent feeling, while maintaining a function of adsorbing and removing an excreted waste product. However, although an effect of the lasting cosmetic quality can be expected, no consideration is made of enhancement of the dispersibility among fine particles exhibiting an UV shielding effect or the prevention of re-flocculation with the lapse of time. In addition, the production costs of these powders are high. (Patent Documents 3 and 4)

Furthermore, in order to improve the lasting cosmetic quality and enhance water repellency and oil repellency against sweat and sebum, cosmetics containing fluorine-treated powders are proposed. Although the cosmetics using the powder are less wetted with the skin and sweat, an attachment amount to the skin is small because the water repellency and the oil repellency are high. Consequently, a phenomenon that the powder slides on the skin to <twist> a cosmetic film is seen, so that a make-up effect is damaged. Moreover, fluorine compounds such as a perfluoroalkyl phosphoric acid ester diethanolamine salt and the like contain a diethanolamine which is unfavorable from a standpoint of safety. There is a problem that producing steps becomes complicated so as to remove this. (Patent Document 5)

PRIOR ART DOCUMENTS

Patent Documents

[Patent Document 1] JP-A 3-279323
[Patent Document 2] JP-A 9-301828
[Patent Document 3] JP-A 2004-315467
[Patent Document 4] JP-A 2006-327961
[Patent Document 5] JP-A S62-250074

SUMMARY OF THE INVENTION

Problems to be Solved by the Invention

The present invention is aimed at providing a composition for cosmetics and cosmetics, which have good dispersibility and a high UV shielding effect, maintain cosmetic effects thereof, have good use feeling, an UV shielding effect and a sebum solidifying ability.

Measures to Solve the Problems (1) The present invention is directed to a composition for cosmetics, which composition is characterized by comprising at least (A) microparticulate titanium dioxide (a first ingredient), and (B) one kind or two or more kinds of magnesium oxide, calcium oxide, magnesium hydroxide and calcium hydroxide (a second ingredient). In this connection, "comprising at least" includes a case in which the "composition for cosmetic" may not only consist of the first ingredient (A) and the second ingredient (B) only, but also a case in which other ingredient is contained besides (A) and (B) so long as the object and the effect of the invention are accomplished without being hindered.

(2) The present invention is directed to a composition for cosmetics, which composition is characterized by comprising at least (A) microparticulate titanium dioxide (a first ingredient), (B) one kind or two or more kinds of magnesium oxide, calcium oxide, magnesium hydroxide and calcium hydroxide (a second ingredient), and (C) a clay mineral (a third ingredient). In this connection, "comprising at least" includes a case in which the "composition for a cosmetic preparation" may not only consist of the first ingredient (A), the second ingredient (B) and the third ingredient (C) only, but also a case in which other ingredient is contained besides (A), (B) and (C) so long as the object and the effect of the invention are accomplished without being hindered.

In the following, preferred examples of the present invention are described, but any combinations thereof are examples of the present invention so long as there is no particular contradiction.

(3) The compounding weight rate among (A) microparticulate titanium dioxide (a first ingredient), (B) one kind or two or more kinds of magnesium oxide, calcium oxide, magnesium hydroxide and calcium hydroxide (a second ingredient), and (C) the clay mineral (a third ingredient) is 20 to 97:3 to 40:0 to 77.

(4) The composition for cosmetics is lipophilically treated with a lipophilizing agent (D).

(5) The lipophilizing agent is one kind of a compound or a mixture of two or more kinds of compounds selected from an alkyl alkoxy silane represented by the following general formula (1), a reactive organosilicone represented by the following general formula (2), an acylated amino acid (including one in the form of a salt), a polyolefin, hydrogenated lecithin, dextrine fatty acid ester, a fluorine compound containing a perfluoroalkyl group or a perfluoropolyether group, and a saturated or unsaturated fatty acid having 12 to 22 carbon atoms (including ones in the form of a salt).

(Chemical formula 1)

wherein n is an integer of 1 to 18, m is an integer of 1 to 3, a and b represent an integer of 1 to 3, and a+b=4.

(Chemical formula 2)

wherein all of $R^1$s are mutually independent, and represent a lower alkyl group having 1 to 4 carbon atoms or a hydrogen atom, respectively, $R^2$ represents any of an amino group, a hydrogen atom, a hydroxyl group and a lower alkoxy group having 1 to 4 carbon atoms, and p is an integer of 1 to 300.

(6) The lipophilizing agent is one kind of a compound or a mixture of two or more kinds of compounds selected from an alkyl alkoxy silane represented by the following general formula (1), a reactive organosilicone represented by the following general formula (2) and an acylated amino acid, and a saturated or unsaturated fatty acid having 12 to 22 carbon atoms (including one in the form of a salt).

(Chemical formula 3)

wherein n is an integer of 1 to 18, m is an integer of 1 to 3, a, b represent an integer of 1 to 3 and a+b=4.

(Chemical formula 4)

wherein all of R1s are mutually independent, and represent a lower alkyl group having 1 to 4 carbon atoms or a hydrogen atom, respectively, R2 represents any of an amino group, a hydrogen atom, a hydroxyl group and a lower alkoxy group having 1 to 4 carbon atoms, and p is an integer of 1 to 300.

(7) The composition for cosmetics is one which is obtained by mixing (A) the microparticulate titanium dioxide and (B) one kind or two or more kinds of magnesium oxide, calcium oxide, magnesium hydroxide and calcium hydroxide, thereafter pulverizing or crushing the mixture with a jet air stream, and simultaneously adsorbing or bonding the lipophilizing agent onto the resultant.

(8) The composition for cosmetics is one which is obtained by mixing (A) the microparticulate titanium dioxide and (B) one kind or two or more kinds of magnesium oxide, calcium oxide, magnesium hydroxide and calcium hydroxide, or mixing (A) the microparticulate titanium dioxide, (B) one kind or two or more kinds of magnesium oxide, calcium oxide, magnesium hydroxide and calcium hydroxide, and (C) a clay mineral, thereafter pulverizing or crushing the mixture with a jet air stream, and simultaneously adsorbing or bonding the lipophilizing agent onto the resultant.

(9) The present invention is directed to a cosmetic containing the composition for cosmetics described in any of the above (1) to (8). Preferably, 0.5 to 50 wt % of the above composition for cosmetics is contained relative to the total weight of the cosmetic.

Effects of the Invention

The present invention can provide the cosmetic, which has good dispersibility, excellently high UV shielding effect, and excellent use feeling, long-lasting cosmetic effect, by incorporating into the cosmetic the composition for cosmetics which contains at least microparticulate titanium dioxide (a first ingredient), and one kind or two or more kinds of magnesium oxide, calcium oxide, magnesium hydroxide and calcium hydroxide (a second ingredient). In addition, when the clay mineral (third ingredient) is contained, the UV shielding effect and the use feeling are further improved.

EXAMPLES TO CARRY OUT THE INVENTION

In the following, the present invention will be explained in detail, but the invention is not limited thereto.

(1) Microparticulate Titanium Dioxide

In the present invention, microparticulate titanium dioxide functions to afford the UV shielding effect. As primary particle diameters of miroparticulate titanium dioxide, a few Å to 200 um are recited. As to the microparticulate titanium dioxide suitable for the present invention, the primary particle diameters are preferably in a range of 10 to 200 nm. More preferably, the primary particle diameters are 10 to 120 nm. Since titanium dioxide having particle diameters of 200 nm or more have lower UV shielding effect and low transparency, it becomes too whitish. Further, if the particle diameters are not more than 10 nm, the UV-B waves in 290 to 320 nm which cause erythema or inflammation are allowed to pass, the UV shielding effect is low. Further, there are an amorphous shape, a spindle-like shape, a butterfly-like shape, a cocoon-like shape and the like as the shapes of the particles, and any shape of them may specifically do. Furthermore, as the crystalline structure, there are a rutile structure, an anatase structure and a rutile/anatase structure, and any crystalline structure of them may do.

Meanwhile, since the microparticulate titanium dioxide has very a high surface activity, surfaces of the particles are preferably inorganically treated. As the inorganic treatment, the particles are preferably treated with one kind or two or more kinds of silica, alumina, aluminum hydroxide, zirconia and the like. Further, as microparticulate titanium dioxide, there are ones colored by doping a metal such as Fe, Mg or the like, for example. In the present invention, they can be used, and they are included in the "microparticulate titanium dioxide" in the present invention.

(2) Magnesium Oxide, Calcium Oxide, Magnesium Hydroxide and Calcium Hydroxide

Magnesium oxide, calcium oxide, magnesium hydroxide and calcium hydroxide improve the long-lasting cosmetic effect and afford convergent, anti-inflammatory and antibacterial functions through the solidification of sebum. As usable magnesium oxide, (a) it can be obtained by heating metallic magnesium in the atmosphere or (b) it can be obtained by thermally decomposing at least any one kind of magnesium carbonate, magnesium hydroxycarbonate and magnesium hydroxide. Meanwhile, calcium oxide, which is ordinarily commercially available, can be obtained (a) by calcining any one or more kinds of a carbonate salt as well as a nitrate salt, an oxalate salt and a hydroxide calcium, alternatively it can be obtained (b) by placing pure calcium nitrate in a quartz crucible and completely decomposing it in an electric furnace or the like. A variety of producing methods are available for magnetic oxide, calcium oxide, magnesium hydroxide and calcium hydroxide. Those usable in the present invention are not limited to those produced by the producing methods given above.

Furthermore, when magnesium oxide, calcium oxide, magnesium hydroxide and/or calcium oxide is mixed, pH values of some cosmetics need to be lowered. In this case, they can be neutralized with an organic acid or the like. As the organic acid, there are acetic acid, tartaric acid, lactic acid, an acylated amino acid, an amino acid, citric acid, glutamic acid and the like.

(3) Mineral Clay

The clay mineral in the present invention functions to stably disperse microparticulate titanium dioxide, magnesium oxide, calcium oxide, magnesium hydroxide, calcium hydroxide, etc., prevent re-flocculation and improve the use feeling of the cosmetics. As the clay mineral suitable for the present invention, no limitation is posed upon it, so long as it can be used as a powder to be employed in ordinary cosmetics. For example, there are boron nitride, sericite, natural mica, calcined mica, synthetic mica, synthetic sericite, alumina, mica, talc, kaolin, bentonite, smectite and so on. As to particle sizes thereof, the average particle size of 1 to 25 µm (laser method) is preferred. If it is smaller than 1 µm, feeling is bad, whereas if it is larger than 25 µm, the specific surface area becomes extremely smaller, so that it is likely that the clay mineral does not fulfill a role to improve the dispersibility of one kind or one or more kinds of the microparticulate titanium dioxide and magnesium oxide, and calcium oxide, magnesium hydroxide and calcium hydroxide. Methods for producing such clay minerals are not limited, and the clay minerals are preferably as thin planar particles as possible. The aspect ratio (major axis of the particle/particle thickness) is preferably 2 to 200, and more preferably 5 to 100.

(4) Mixing Ratio

The mixing weight ratio among the microparticulate titanium dioxide (first ingredient), one kind or two or more kinds of magnesium oxide, calcium oxide, magnesium hydroxide and calcium hydroxide (second ingredient) and the clay mineral (third ingredient) is 20 to 97:3 to 40:0 to 77. It is preferably 25 to 50:5 to 35:30 to 70. If the weight rate of the microparticulate titanium dioxide (first ingredient) is lower outside this range, the UV shielding effect is low. If the weight rate of magnesium oxide, calcium oxide, magnesium hydroxide, calcium hydroxide and the like (second ingredient) is lower, the lasting cosmetic effect is lowered, whereas if it is higher, stability of the cosmetics may be damaged. Further, regarding the weight rate of the clay mineral (third ingredient), even if the clay mineral (third ingredient) is not contained, the UV shielding effect and the lasting cosmetic performance based on the sebum solidifying ability can be exhibited, but the clay mineral (third ingredient) is preferably contained, because the UV shielding effect and the use feeling are better. If the weight rate is outside that range, the rates of the other ingredients become smaller, the UV shielding effect is lowered, the sebum solidifying ability is deteriorated, and the lasting cosmetic effect decreases.

(5) Configuration of the Composition

When an example of the composition for cosmetics according to the present invention is observed with a scanning electron microscope, flocculated particles in which some small particles are flocculated are observed in a case of a composition for cosmetics in which no clay mineral is contained. They are present as weakly flocculated blocks, and when a cosmetic containing a composition for cosmetics according to the present invention is produced, flocculated blocks are broken and dispersed during the production of the cosmetic. Further, when a clay mineral is contained, a mixture of secondary flocculated particles in which some small particles (microparticulate titanium dioxide and calcium oxide, magnesium hydroxide, calcium hydroxide and so on) are attached and solidified onto surfaces of flocculated aggregated particles is observed. Particles in which no small particles are attached or solidified on the surface of the clay mineral are scattered, but present as weakly flocculated bodies, so that the flocculated bodies are broken and dispersed during the production of a cosmetic, when the cosmetic containing the composition for cosmetics according to the present invention is produced. Attachment and solidification mentioned here mean that when such secondary flocculated particles are put, stirred and dispersed in a test tube containing decamethylpentasiloxane to be used in a cosmetic, for example, small particles leave from the surface of the clay mineral and puddle a supernatant liquid in the case of the attachment, while only the clay mineral settles down, whereas in the case of the solidification, small particles on the surface of the clay mineral all settle down without leaving therefrom, and the supernatant liquid is transparent. Further, the clay mineral serves as a dispersing assistance of the microparticulate titanium dioxide, magnesium oxide and so on and plays a role to prevent re-flocculation with the lapse of time. The greater the mixing rate of the clay mineral, the more are the secondary flocculated particles in which the microp articulate titanium dioxide, magnesium oxide and so on are attached or solidified on the surface of the clay mineral, so that there is a tendency that the UV shielding effect increases and the use feeling is improved. However, since the mixing rates of the microparticulate titanium dioxide, magnesium oxide and so on decreases, they are preferably set at the mixing rates in (4) mentioned above.

(6) Lipophilization Surface-Treating Agent

According to the present invention, a powder is surface-treated with a lipophilization surface-treating agent composed of one kind of a compound or a mixture of two or more kinds of compounds selected from an alkyl alkoxy silane represented by the following general formula (1), a reactive organosilicone represented by the following general formula (2), an acylated amino acid (containing one in the form of a salt), a polyolefin, hydrogenated lecithin, dextrin fatty acid ester, a fluorine compound containing a perfluoroalkyl group or a perfluoropolyether group, a saturated or unsaturated fatty acid having 12 to 22 carbon atoms (including one in the form of a salt).

(Chemical formula 5)

$$(C_nH_{2n+1})_a Si(OC_mH_{2m+1})_b \quad (1)$$

wherein n is an integer of 1 to 18, m is an integer of 1 to 3, a, b denote an integer of 1 to 3, and a+b=4.

(Chemical formula 6)

$$(R^1{}_3SiO)(R^1{}_2SiO)_p(SiR^2{}_3) \quad (2)$$

wherein all of R1s are mutually independent, and represent a lower alkyl group having 1 to 4 carbon atoms or a hydrogen atom, respectively, R2 represents any of an amino group, a hydrogen atom, a hydroxyl group and a lower alkoxy group having 1 to 4 carbon atoms, and p is an integer of 1 to 300.

The acrylated amino acid is one in which an amino group and an imino group of the amino acid are acylated. As the amino acid constituting the acylated amino acid, one kind of an amino acid and a mixture of plural kinds of amino acids may do. When there are an L-configuration, a D-configuration and a DL-configuration in the amino acid constituting the acylated amino acid, any of the isomers may do or a mixture of the plural configurations may do. The L-configuration present in natural is more preferable.

As kinds of the amino acids, glycine, alanine, balin, leucine, iso-leucine, phenylalanine, Proline, threonine, serine, arginine, lysine, aspartic acid, glutamic acid, tyrosine, methionine, cystine, cysteine and the like can be recited.

As the fatty acid constituting the acylated product, a saturated or unsaturated fatty acid preferably 1 to 23 carbon atoms or a fatty acid having a saturated or unsaturated alicyclic structure with 1 to 23 carbon atoms can be recited. For example, N-acylated glycine, N-acylated-N-methyl-β-alanine, N-acylated glutamic acid, salts thereof and so on can be recited. (JP-A 61-73775)

As the constituent fatty acid, a long-chain fatty acid is preferable. For example, caprylic acid, capric acid, lauric acid, myristic acid, isomyristic acid, stearic acid, isostearic acid, arachin acid, oleic acid, myristoleic acid, linoic acid, linoleic acid, arachidonic acid and coconut oil fatty acid and so on can be recited.

The acylated amino acid can be used in the form of a free state or a salt. As the salt form, metal salts of such as Na, K, Ba, Zn, Ca, Mg, Fe, Zr, Co, Al, Zr, Ti and the like, various alkane amine salts such as an ammonium salt, a mono-ethanol amine, diethanolamine, triethanolamine, 2-amino-2-methyl-propanol, 2-amino-2-methyl-1,3-propanediol, triisopropanolamine and so on can be recited.

For example, as those easily commercially available and usable, there are alanine N-acylated with coconut oil fatty acid or N-lauroyl-β-alanine (Kawaken Fine Chemicals Co., Ltd.) and Ca and Al salts thereof, a myristoyl silk amino acid (PHYTOCOS CO., Ltd.) and its Al salt, N-lauroyl-L-lysine and N-stearoyl-L-glutamic acid (AJINOMOTO HEALTHY SUPPLY, INC.), an Na salt of a condensation product between N-lauroyl-L-glutamic acid and lysine (Asahi Kasei Chemicals Corporation) and so on.

As the fatty acid, the fatty acids explained in connection with those constituting the above acylated amino acids may be employed. As salt forms, the salts explained in the case that the above acylated amino acids are in the form of the salts are employed. Particularly, the saturated or non-saturated fatty acid having 12 to 22 carbon atoms (including those in the form of salts) are preferable. For example, fatty acids such as lauryl acid, myristic acid, palmitic acid, stearic acid, behenic acid, lignoceric acid, cerotinic acid and so on, or Na, Ca, Mg, Zn, Al and Ti thereof are preferable.

Furthermore, as other lipophilization surface-treating agents, a polyolefin, hydrogenated lecithin, dextrin fatty acid ester, a fluorine compound having a perfluoroalkyl group or a perfluoropolyether group and so on can be appropriately selectively used depending upon the kind and the composition of a cosmetic preparation to be mixed with.

(7) Lipophilization Surface-Treating Method

As a method for lipophilization surface-treating a powder with a lipophilization surface-treating agent, a publicly known method has only to be used. A powder can be surface-treated for lipophilization by mixing and contacting the powder with the lipophilization surface-treating agent to be used in the present invention for a given time period. In the case that the lipophilization surface-treating agent is mixed and contacted with the powder, this step may be performed (a) after the microparticulate titanium dioxide, (the clay mineral) and one kind or two or more kinds of magnesium oxide, calcium oxide, magnesium hydroxide and calcium hydroxide are mixed, or (b) it may be performed simultaneously with mixing the powders, or (c) the mixing may be performed after the respective powders are separately surface-treated for lipophilization. The most preferable method is that after the respective ingredient powders are preliminarily mixed, the resultant is mixed and contacted with the lipophilization surface-treating agent.

Further, there is a method in which after the powder is surface-treated for lipophilization, the resultant is crushed with a jet mill. As the method in which after the powder is surface-treated for lipophilization, the resultant is crushed with the jet mill pulverizer, the following two methods are recited, for example. (1) After the lipophilization surface-treating agent and the powder are dry or wet mixed and dispersed, the resultant is pulverized with the jet mill pulverizer, and then dried under heating. (2) After the lipophilization surface-treating agent and the powder are dry or wet mixed and dispersed and dried under heating, the resultant is pulverized with the jet mill pulverizer. In case that a powder having primary particle sizes of submicrons or more is coated, a pulverizer such as a pin mill, a hammer mill or the like may be used instead of the jet mill pulverizer.

As a mixing dispersion device to be used for mixing and contacting the above powders, a Henschel mixer. a ribbon blender, a Q mill, a kneader, a planetary mixer, a pony mixer, a Bumbary mixer, a ball mill, a dry-type sand mill, a wet-type sand mill, an attritor, a hybridizer, a Disper mixer, a homo mixer, an extruder and the like are recited. Further, this treatment may be carried out, while an energy such as a mechanochemical mechanical force, ultrasonic waves, plasma, flame, UV rays, electron beams, overheated steam or the like is being applied.

In order to complete the reaction between the lipophilization surface-treating agent and the surfaces of the powder particles with respect to the powder lipophilization surface-treated by the above mixing dispersion device, the powder is heated at a temperature of 100° C. to 170° C. for 3 hours to 20 hours, for example.

As a particularly preferable example in this explanation, it is recited that after the powders are mixed and contacted, the powder lipophilically surface-treated is pulverized by using the jet mill pulverizer. In this case, the performances such as the UV shielding effect, the feeling, etc. are further improved by reducing coarse particles and sharpening the particle size distribution. The jet mill pulverizer is broadly classified into a flowing layer type, a spiral type, a jet automizer type and the like. Although any type may be used, the flowing layer type which can uniformly and effectively carry out the treatment is most preferable.

A jet stream is ejected through one or plural ejecting holes or ejecting nozzles provided inside the pulverizer. A gas to be used as the jet stream, air, a nitrogen gas, a helium gas, steam and the like are recited, and it may be selected depending upon the powder to be treated and the properties of the surface-treating agent.

When air is used as the gas and blown to the treating object through the nozzle, the pressure at an exit of the nozzle is preferably 0.4 to 2.0 MPa, more preferably a pressure of 0.6 MPa or more is used.

In this pulverizer, the mixed powders are stirred, while being fluidized inside the pulverizer, particles are collided with one another by using the nozzle exit pressure of 0.6 MPa or more, the powders are pulverized and crushed with the energy thereof, and simultaneously the surface-treating agent is uniformly solidified, adsorbed and bonded onto the surfaces of the powder having a large surface area. Therefore, the lipophilization surface-treating agent is uniformly adsorbed and bonded onto the surface of the powder without being contaminated with another substance and before the secondary flocculation of the powdery particles takes place.

As a condition for pulverizing the powder, a feeding amount of the powder and a nozzle diameter and the number of classifying rotations may be set, besides the above nozzle pressure, depending upon the kinds of the respectively microparticulate powders, the kind of the lipophilization surface-treating agent and a treating amount. The mixing weight ratio between the powder to be treated and the lipophilization surface-treating agent is preferably that the lipophilization surface-treating agent is 0 to 30 parts by weight relative to 100 parts by weight of the powder. Regarding the cosmetic in which the powder needs to be surface-treated for lipophilization, the lipophilization surface-treating agent is preferably 1 to 10 parts by weight relative to 100 parts by weight of the powder. Although different depending upon the kind of the powder, the primary particle diameters, the specific surface area, the oil absorbing amount, etc., if the lipophilization surface-treating agent exceeds the above ratio, there is a tendency that the dispersibility becomes worse, the UV shielding effect decreases, and the use feeling is deteriorated. Depending on the cosmetics, they may be used without the lipophilizing treatment. Meanwhile, the mixing ratio among two or more kinds of lipophilization surface-treating agents is not particularly limited.

(8) Cosmetics

No particular limitation is imposed upon cosmetics into which the composition for cosmetics according to the present invention is mixed. Although the mixing weight % of the above composition for cosmetics varies depending on the kind of the formulations of the cosmetics, the above composition for cosmetics can be added in 0.5 to 50 wt % relative to the total weight of the cosmetic. As the formulations of the cosmetics, for example, conventionally publicly known formulations such as an emulsion form, a creamy form, a solid form, a paste form, a gel form, a powdery form, a multilayer form, a mousse form, a spray form, etc. can be selected. Specifically, recitation can be made of, as makeup cosmetics, a makeup base, a powder foundation, a liquid foundation, an oily foundation, a stick foundation, pressed powder, a face powder, a white powder, a lip stick, a lip stick overcoat, a lip gloss, a concealer, a blusher, an eye shadow, an eyebrow, an eyeliner, a mascara, an aqueous nail enamel, an oily nail enamel, an emulsion type nail enamel, an enamel top coat, an enamel base coat and the like; as skincare cosmetics, an emollient cream, a cold cream, a whitening cream, an emulsion, a lotion, a beauty essence, a carmine lotion, a body gloss, ultraviolet control cosmetics such as a sun block, a sunburn cream and the like, a lotion and the like; as hair cosmetics, a hair gloss, a hair cream, a hair shampoo, a hair rinse, a hair color, a hair brushing agent and the like; as antiperspirant cosmetics, a cream, lotion, a powder, a spray type deodorant product and the like; and all cosmetics to which the UV protective effect is afforded.

The cosmetics in which the cosmetic composition of the present invention is mixed can be appropriately blended with a pigment dispersant, an oily agent, a surface active agent, UV absorber, an antiseptic, an antioxidant, a film former, a moisturizer, a thickener, a dye, an antiseptic, a pigment, a perfume, etc., which are usually used in the cosmetics and the like, so long as they do not damage the effects of the present invention.

Furthermore, the thus obtained surface-treated inorganic powders can be used as powders to be used widely over various fields for not only cosmetics but also additives to the plastics, inks, paints, toners (magnetic powders), chemical fibers, wrapping materials, electronic material and so on.

EXAMPLES

In the following, the present invention will be explained in detail by taking examples and evaluation test methods, but the present invention is not limited to these examples.

Example 1

In a Q mill (manufactured by NIPPON COKE & ENGINEERING. CO., LTD.: Multi-purpose mixer), 50 g of a surface-treating agent: methyl hydrogen polysiloxane (manufactured by SHIN-ETSU CHEMICAL CO., LTD.: KF-99P) was fed into 1 kg of microparticulate titanium dioxide (manufactured by ISHIHARA SANGYO KAISHA, LTD: TTO-55A), 0.3 kg of talc (manufactured by MIYOSHI KASEI INC.: Soft Talc), 0.7 kg of magnesium oxide (manufactured by TOMITA PHARMACEUTICAL CO., LTD.), while the latter was being mixed under stirring, and stirring was performed for 10 minutes. Then, after the mixture was pulverized in a jet mill (manufactured by ALPINE AG, Germany: 100AFG type) under the condition of a pulverizing pressure: 0.6 MPa and the number of classifying rotations: 7000 rpm, the resultant was dried in a hot air drier at 130° C. for 12 hours, thereby obtaining a lipophilically surface-treated composition.

Example 2

In a henschel mixer (manufactured by NIPPON COKE & ENGINEERING. CO., LTD.: FM), 50 g of a surface-treating agent: methyl hydrogen polysiloxane (manufactured by SHIN-ETSU CHEMICAL CO., LTD.: KF-99P) was fed into 1 kg of microparticulate titanium dioxide (manufactured by ISHIHARA SANGYO KAISHA, LTD: TTO-51A), 0.8 kg of talc (manufactured by ASADA MILLING CO., LTD.: JA-13R), 0.1 kg of magnesium oxide (manufactured by TOMITA PHARMACEUTICAL CO., LTD.) and 0.1 kg of calcium oxide (reagent), while the latter was being mixed under stirring, and stirring was performed for 10 minutes. Then, after the mixture was pulverized in a jet mill (manufactured by ALPINE AG, Germany: 100AFG type) under the condition of a pulverizing pressure: 0.6 MPa and the number of classifying rotations: 7000 rpm, the resultant was dried in the hot air drier at 130° C. for 12 hours, thereby obtaining a lipophilically surface-treated composition.

Example 3

In a Q mill (manufactured by NIPPON COKE & ENGINEERING. CO., LTD.: Multi-purpose mixer), 50 g of a surface-treating agent: methyl hydrogen polysiloxane (manufactured by SHIN-ETSU CHEMICAL CO., LTD.: KF-9901) was fed into 1 kg of microparticulate titanium dioxide (manufactured by ISHIHARA SANGYO KAISHA, LTD: TTO-55A), 0.8 kg of talc (manufactured by MIYOSHI KASEI INC.: Soft Talc) and 0.2 kg of magnesium oxide (manufactured by TOMITA PHARMACEUTICAL CO., LTD.), while the latter was being mixed under stirring, and stirring was performed for 10 minutes. Then, the mixture was dried in a hot air drier at 110° C. for 12 hours, thereby obtaining a lipophilically surface-treated composition.

Example 4

Into a henschel mixer (manufactured by NIPPON COKE & ENGINEERING. CO., LTD.: FM) were put 2 kg of microparticulate titanium dioxide (manufactured by ISHIHARA SANGYO KAISHA, LTD: TTO-55A) and 50 g of a surface-treating agent: methyl hydrogen polysiloxane (manufactured by SHIN-ETSU CHEMICAL CO., LTD.: KF-9901) and stirring was performed for 10 minutes. Then, after the mixture was pulverized in a jet mill (manufactured by ALPINE AG, Germany: 100AFG type) under the condition of a pulverizing pressure: 0.6 MPa and the number of classifying rotations: 7000 rpm, the resultant was dried in the hot air drier at 110° C. for 9 hours. Under the same condition, talc (manufactured by MIYOSHI KASEI, INC.: Soft Talc), and magnesium oxide (manufactured by TOMITA PHARMACEUTICAL CO., LTD.) were treated, and 1 kg of the treated microparticulate titanium dioxide, 0.6 kg of the treated SOFT TALC, and 0.4 kg of the treated magnesium oxide were mixed in the henschel mixer for 10 minutes under stirring, thereby obtaining a lipophilically surface-treated composition.

Example 5

In a planetary mixer (manufactured by INOUE MFG., INC.), a liquid in which 80 g of a surface-treating agent: an acylated amino acid (manufactured by AJINOMOTO HEALTHY SUPPLY, INC.: HS-21P) was dissolved with 200 g of heated ion-exchanged water was fed into 1 kg of microparticulate titanium dioxide (manufactured by ISHIHARA SANGYO KAISHA, LTD.: TTO-55A), 0.8 kg of sericite (SANSHIN KOUKOU CO., LTD.: Sericite FSE), 0.2 kg of calcium oxide (reagent), and 0.9 kg of ion-exchanged water, while the latter was being mixed under stirring. After kneaded for 10 minutes, 140 g of a 20% aqueous solution of aluminum sulfate was fed to the resultant, the mixture was mixed for 10 minutes. Then, after the mixture was dried in a hot air drier at 120° C. for 16 hours, the resultant was pulverized in a jet mill (manufactured by ALPINE AG, Germany: 100AFG type) under the condition of a pulverizing pressure: 0.6 MPa and the number of classifying rotations: 10000 rpm, thereby obtaining a lipophilically surface-treated composition.

Example 6

A lipophilically surface-treated composition was obtained by replacing the surface-treating agent in Example 4 with a C6 fluorine acrylate/polyalkylene glycol acrylate copolymer (Daikin Industries, Ltd.).

Example 7 n-Paraffin (manufactured by Nippon Oil Corporation: No. 0 Solvent), 3 kg, was placed and heated to 80° C. in a vessel, and 150 g of a surface-treating agent: myristic acid (manufactured by KAO CORPORATION: MY-98) was dissolved thereinto under stirring with a Disper. Then, a mixture of 1.1 kg of microparticulate titanium dioxide ((manufactured by ISHIHARA SANGYO KAISHA, LTD.: TTO-80A), 3.5 kg of talc (manufactured by MIYOSHI KASEI, INC.: Soft Talc) and 0.4 kg of magnesium oxide (manufactured by TOMITA PHARMACEUTICAL CO., LTD.) was fed to the solution, and after stirring for 60 minutes, n-paraffin was removed in the planetary mixer by heating under a reduced pressure (80° C. to 120° C., 700 mmHg), and then the residue was dried in the hot air drier at 120° C. for 9 hours. Next, after the mixture was pulverized in the jet mill (manufactured by ALPINE AG, Germany: 100AFG type) under the condition of a pulverizing pressure: 0.6 MPa and the number of classifying rotations: 7000 rpm, thereby obtaining a lipophilically surface-treated composition.

Example 8

In a pony mixer, 150 g of a surface-treating agent: myristic acid (manufactured by KAO CORPORATION: MY-98) and 50 g of octyl triethoxy silane (manufactured by Momentive Performance Materials Inc.: A-137) were fed into 1.1 kg of microparticulate titanium dioxide ((manufactured by ISHIHARA SANGYO KAISHA, LTD.: TTO-80A), 3.5 kg of talc (manufactured by MIYOSHI KASEI, INC.: Soft Talc) and 0.4 kg of magnesium oxide (manufactured by TOMITA PHARMACEUTICAL CO., LTD.), while the latter was being mixed under stirring, and the mixture was stirred for 60 minutes. Then, after the mixture was pulverized in the jet mill (manufactured by ALPINE AG, Germany: 100AFG type) under the condition of a pulverizing pressure: 0.6 MPa and the number of classifying rotations: 7000 rpm, the resultant was dried in the hot air drier at 110° C. for 9 hours, thereby obtaining a lipophilically surface-treated composition.

Example 9

In the Q mill (manufactured by NIPPON COKE & ENGINEERING. CO., LTD.: Multi-purpose mixer), 120 g of a surface-treating agent: methyl hydrogen polysiloxane (manufactured by SHIN-ETSU CHEMICAL CO., LTD.: KF-99P) was fed into 1.6 kg of microparticulate titanium dioxide (manufactured by ISHIHARA SANGYO KAISHA, LTD: TTO-55A) and 0.4 kg of magnesium oxide (manufactured by TOMITA PHARMACEUTICAL CO., LTD.), while the latter was being mixed under stirring, and stirring was performed for 10 minutes. Then, after the mixture was pulverized in the jet mill (manufactured by ALPINE AG, Germany: 100AFG type) under the condition of a pulverizing pressure: 0.6 MPa and the number of classifying rotations: 7000 rpm, the resultant was dried in the hot air drier at 110° C. for 9 hours, thereby obtaining a lipophilically surface-treated composition.

Comparative Example 1

In the Q mill (manufactured by NIPPON COKE & ENGINEERING CO., LTD.: Multi-purpose mixer), 50 g of the surface-treating agent: methyl hydrogen polysiloxane (manufactured by SHIN-ETSU CHEMICAL CO., LTD.: KF-9901) was fed into 1 kg of microparticulate titanium dioxide (manufactured by ISHIHARA SANGYO KAISHA, LTD: TTO-55A) and 1 kg of talc (manufactured by ASADA MILLING CO., LTD.: JA-13R), while the latter was being mixed under heating, and then stirring was carried out for 10 minutes. Then, after the mixture was pulverized in the jet mill (manufactured by ALPINE AG, Germany: 100AFG type) under the condition of a pulverizing pressure: 0.6 MPa and the number of classifying rotations: 7000 rpm, the resultant was dried in the hot air drier at 110° C. for 9 hours, thereby obtaining a lipophilically surface-treated composition.

(Testing/Evaluating Methods)

(1) Hydrophobizing Test Method:

In a 100 cc-beaker, 80 cc of purified water was placed, and about 0.5 g of a sample was fed thereinto, followed by stirring 50 times with a spatula. The turbidity of the purified water at that time was visually judged according to 5 levels. (Evaluation level 5: State in which all powder floats on water surface, while a water phase is completely transparent. Evaluation level 4: State between Evaluation level 5 and Evaluation level 3. Evaluation level 3: State in which a part of powder floats on water surface, while water phase is cloudy. Evaluation level 2: State between Evaluation level 3 and Evaluation level 1 Evaluation 1: State in which all powder sets in water and water is cloudy) Next, Stirring is carried out again 50 times with a spatula, a similar operation is repeated totally three times, and evaluation is made.

(2) Solidifying Test Method:

A mixed solution of oleic acid: ethanol: water=20 wt %:78 wt %:2 wt % was prepared, 10 g of this mixed solution was measured in a sample bottle, and 3 g of an evaluation sample was fed. Thereafter, it is shaken 20 times by hand, then placed still at room temperature, and a solidifying time of the mixed solution is measured.

(3) UV Shielding Effect-Measuring Method (In-Vitro SPF, UVA-PA)

UV shielding effect was measured with an SPF analyzer (Optometrics Corporation SPF-290). The measuring method is that a Transpore surgical tape of 3M CO., LTD. was put on a quartz plate, and 1.5 mg/cm2 was applied in case of a powder type and 2.0 mg/cm2 in case of a liquid type with a sponge puff. The UV shielding effects were at 9 locations by using the SPF analyzer, and the average values thereof were taken as an in-vitro SPF value and a PFA value. As to some samples, the above operations were repeated, and the average values were taken.

(4) Evaluation of Use Feeling

A lipophilically surface-treated composition to be evaluated was attached to a finger, and as to a feeling at the time when it was rubbed against a skin, averages of results from 10 panelists were taken according to the following criteria. ⊚ smooth and easily spread, ○ smooth, Δ slightly rough feeling, X rough feeling.

TABLE 1

Table 1: Evaluation of compositions alone

|  | Lipophilization | Solidifying | UV shielding test | |
|---|---|---|---|---|
|  | Use feeling | test 1st-2nd-3rd | test (min) | In-Vitro SPF value | UVA-PF |
| Example 1 | ⊚ | 5-5-5 | 20 | 16 | 7.0 |
| Example 2 | ⊚ | 5-5-5 | 60 | 17 | 7.0 |
| Example 3 | ○ | 5-5-5 | 50 | 15 | 6.8 |
| Example 4 | ○ | 2-2-1 | 240 | 14 | 5.8 |
| Example 5 | ⊚ | 5-5-5 | 40 | 16 | 7.0 |
| Example 6 | ⊚ | 5-5-5 | 60 | 15 | 6.9 |
| Example 7 | ⊚ | 5-5-5 | 120 | 25 | 12.0 |
| Example 8 | ⊚ | 5-5-5 | 120 | 27 | 14.0 |
| Example 9 | Δ | 4-3-3 | 30 | 17 | 7.0 |
| Com. Exam. 1 | ○ | 5-5-5 | not solidified | 18 | 8.0 |

Evaluations of the compositions alone reveal that the products according to the present invention have high UV shielding effects, excellent use feeling, hydrophobicity and sebum solidifying ability, so that the cosmetics into which the compositions of the present invention are mixed have excellent UV shielding effects, and cosmetics having excellent use feeling, cosmetic effects, long-lasting cosmetic performance and safety can be produced. In the following, these effects of each of the cosmetic preparations were confirmed.

Producing Example 1

Powder Foundation

Powder foundations having a composition shown in Table 2 were produced by the following method.

TABLE 2

Table 2: Producing Example 1

|  | Ingredient | wt. part |
|---|---|---|
| (1) | Talc surface-treated with silicone | 7.7 |
| (2) | Sericite surface-treated with silicone | 38.0 |
| (3) | Example 1, Example 2, Example 7, Comparative Example 1 | 20 |
| (4) | Titanium dioxide surface-treated with silicone | 7.0 |
| (5) | Red iron oxide | 3.0 |
| (6) | Yellow iron oxide surface-treated with silicone | 1.0 |
| (7) | Black iron oxide surface-treated with silicone | 0.6 |
| (8) | Nylon powder | 13.0 |
| (9) | Octyldodecyl oleate | 3.0 |
| (10) | Squalane | 4.0 |
| (11) | Dimethyl polysiloxane | 2.7 |
| (12) | Antisepatic agent | Appro.* amount |
| (13) | Perfume | Appro. amount |

*Appropriate

Producing Method:

The above ingredients (1) to (8) are mixed and crushed through a crusher. The resultant was moved into a high speed blender. Ingredients (9) to (13) were homogeneously mixed under heating, which was added to the crushed powder and further uniformly mixed. The resultant was passed through the crusher, particles having uniform particle sizes were obtained through a sieve, and thereafter the powder was compression molded in an aluminum tray under a surface press pressure of 2 MPa, thereby producing a UV cut powder foundation.

TABLE 3

Table 3: Powder foundation
Measurement results of UV shielding effects in Producing Example 1

|  | Example 1 | Example 2 | Example 7 | Com. Example 1 |
|---|---|---|---|---|
| In-vitro SPF value | 18 | 17 | 32 | 16 |
| UVA-PF value | 10.3 | 10.5 | 24.0 | 9.6 |

The cosmetics into which the composition for cosmetics according to the present invention had high UV shielding effects, and further better use feeling, cosmetic effects and long-lasting cosmetic performance as compared with a Comparison product. (Comparative Example 1 is equivalent in UV shielding effect to the invention products in terms of UV shielding effect, but inferior thereto in terms of the long-lasting cosmetic performance.)

Production Example 2

Production of Emulsion Type Foundations

W/O type liquid foundations having compositions shown in Table 4 were produced by the following method.

TABLE 4

Table 4: Producing Example 2

|  | Ingredient | wt. part |
|---|---|---|
| (1) | Decamethylcyclopentasiloxane | 10.0 |
| (2) | Methylpolysiloxane | 5.0 |
| (3) | Methoxy octyl silicate | 2.0 |
| (4) | Isotridecyl isononanoate | 4.7 |
| (5) | Polyether modified silicone (Shin-Etsu Chemical Co., Ltd., KF-6017)) | 3.0 |
| (6) | Example 1 or Comparative Example 1 | 8.0 |
| (7) | Titanium dioxide treated with silicone | 8.0 |
| (8) | Red iron oxide treated with silicone | 0.3 |
| (9) | Yellow iron oxide treated with silicone | 2.0 |
| (10) | Black iron oxide treated with silicone | 0.2 |
| (11) | Polymethylsilsesquioxane | 15.0 |
| (12) | Glycerin | 1.0 |
| (13) | 1,3-butylene glycol | 5.0 |
| (14) | Sodium chloride | 0.5 |
| (15) | Purified water | up to 100.0 |
| (16) | Antiseptic agent | Appro. amount |
| (17) | Perfume | Appro. amount |

Producing Method:

The above ingredients (6) to (11) were preliminarily mixed and crushed. The mixture of the preliminarily crushed ingredients (6) to (11) was added into an oily phase in which ingredients (1) to (5) were uniformly dissolved and mixed at 70° C., which was uniformly dispersed by a Homo Disper. An aqueous phase in which ingredients (12) to (16) were uniformly mixed and dissolved at 70° C. was gradually added into the above oily phase, which was uniformly dispersed by the homo mixer. Thereafter, the dispersion was cooled, and an ingredient (17) was added to adjust emulsified particles, thereby producing a liquid foundation.

The In-vitro SPF value of the cosmetic into which was mixed the cosmetic composition according to the present invention was 35, and that of Comparative product was 25. The cosmetic into which the cosmetic composition according to the present invention was mixed had excellent use feeling, cosmetic effects and lasting cosmetic performance.

Producing Example 3

Production of Emulsion Type Sunscreen Creams

Emulsion type sunscreen creams having the compositions shown in Table 5 were produced by the following method.

TABLE 5

Table 5: Producing Example 3

|  | Ingredient | wt. part |
|---|---|---|
| (1) | Volatile liquid isoparaffin (Isoliexadecane) | 15.0 |
| (2) | Methylpolysiloxane (6cs) | 2.0 |
| (3) | Isotridecyl isononanoate | 3.5 |
| (4) | Cetanol | 1.0 |
| (5) | Squalane | 5.0 |
| (6) | Polyethylene glycol monostearate (4EO) | 1.0 |
| (7) | Hexaglyceryl polyricinoleate | 3.5 |
| (8) | Polyether-modified silicone (Dow Corning Toray Co., Ltd. BY-11-030) | 2.0 |
| (9) | Example 2 or Comparative Example 1 | 10.0 |
| (10) | Purified water | balance |
| (11) | Glycerin | 5.0 |
| (12) | 1,3-butylene glycol | 5.0 |
| (13) | Sodium pyrrolidone carboxylate | 2.5 |
| (14) | Antiseptic agent | Appro. amount |
| (15) | Perfume | Appro. amount |

(Producing Method)

After oily ingredients (1) to (8) was dissolved at 75° C., an ingredient (9) was added into the resultant, which was stirred. Aqueous ingredients (10) to (14) were dissolved at 75° C., homogenized, and added into the oily phase ingredients, which was emulsified by the homo mixer. Finally, an ingredient (15) was added to the resultant, and cooled, thereby producing a sunscreen cream.

The In-vitro SPF value of the cosmetic into which was mixed the cosmetic composition according to the present invention was 15, and that of Comparative product was 12. The cosmetic into which the cosmetic composition according to the present invention was mixed had excellent use feeling, cosmetic effects and lasting cosmetic performance.

Producing Example 6

Production of Emulsions

Emulsions having the compositions shown in FIG. 7 were produced by the following method.

TABLE 6

Table 6: Producing Example 4

|  | Ingredient | wt. part |
|---|---|---|
| (1) | Squalane | 14.0 |
| (2) | Jojoba oil | 4.0 |
| (3) | Olive oil | 2.0 |
| (4) | Cetanol | 0.5 |
| (5) | Vaseline | 1.0 |
| (6) | Bead wax | 0.6 |
| (7) | Sorbitan monostearate | 2.1 |
| (8) | Polyoxyethylene behenyl ether | 2.3 |
| (9) | Butylparaben | 0.1 |
| (10) | Example 1 or Comparative Example 1 | 10.0 |
| (11) | 1,3-butylene glycol | 5.0 |
| (12) | Glycerin | 2.0 |
| (13) | Xanthane gum | 0.14 |
| (14) | Carboxymethyl cellulose sodium salt | 0.1 |
| (15) | Purified water | 56.15 |

(Producing Method)

After oily ingredients (1) to (9) were dissolved at 75° C., an ingredient (10) was added thereto, which was stirred. Aqueous ingredients (11) to (15) were dissolved at 75° C., homogenized and added into the oily ingredients, which was emulsified by the homo mixer and finally cooled, thereby producing a sunscreen cream.

The In-vitro SPF value of the cosmetic into which was mixed the cosmetic composition according to the present invention was 18, and that of Comparative product was 14. The cosmetic into which the lipophilically surface-treated cosmetic composition according to the present invention was mixed had excellent use feeling, cosmetic effects and long-lasting cosmetic performance.

What is claimed is:

1. A composition for cosmetics having a UV shielding effect and a sebum solidifying power, the composition comprising the following components:
   (A) microparticulate titanium dioxide having a primary particle diameter of from 10 to 200 nm; and
   (B) at least one of magnesium oxide, calcium oxide, magnesium hydroxide and calcium hydroxide,
   wherein
   a weight ratio between (A) the microparticulate titanium dioxide and (B) the at least one of magnesium oxide, calcium oxide, magnesium hydroxide and calcium hydroxide is 20-97 : 3-40; and
   the composition is in the form of a mixture of powders, the component (A) and the component (B) each being in powder form.

2. The composition for cosmetics set forth in claim 1, further comprising (C) a clay mineral.

3. The composition for cosmetics set forth in claim 1, wherein the composition for cosmetics is lipophilically treated with (D) a lipophilizing agent.

4. The composition for cosmetics set forth in claim 3, wherein the lipophilizing agent is at least one compound selected from the group consisting of an alkyl alkoxy silane represented by the following general formula (1), a reactive organosilicone represented by the following general formula (2), an acylated amino acid, a polyolefin, hydrogenated lecithin, dextrine fatty acid ester, a compound containing a perfluoroalkyl group or a perfluoropolyether group, and a saturated or unsaturated fatty acid having 12 to 22 carbon atoms (including one in the form of a salt);

$$(C_nH_{2n+1})_aSi(OC_mH_{2m+1})_b \quad (1)$$

wherein n is an integer of 1 to 18, m is an integer of 1 to 3, a and b represent an integer of 1 to 3, and a+b=4, $$(R^1{}_3SiO)(R^1{}_2SiO)_p(SiR^2{}_3) \quad (2)$$

wherein all of $R^1$ s are mutually independent, and represent a lower alkyl group having 1 to 4 carbon atoms or a hydrogen atom, respectively, $R^2$ represents any of an amino group, a hydrogen atom, a hydroxyl group and a lower alkoxy group having 1 to 4 carbon atoms, and p is an integer of 1 to 300.

5. The composition for cosmetics set forth in claim 3, wherein the lipophilizing agent is at least one compound selected from the group consisting of an alkyl alkoxy silane represented by the following general formula (1), a reactive organosilicone represented by the following general formula (2), an acylated amino acid (including one in the form of a salt), and a saturated or unsaturated fatty acid having 12 to 22 carbon atoms (including one, in the form of a salt);

$$(C_nH_{2n+1})_aSi(OC_mH_{2m+1})_b \quad (1)$$

wherein n is an integer of 1 to 18, m is an integer of 1 to 3, a and b represent an integer of 1 to 3, and a+b=4, $$(R^1{}_3SiO)(R^1{}_2SiO)_p(SiR^2{}_3) \quad (2)$$

wherein all of $R^1$ s are mutually independent, and represent a lower alkyl group having 1 to 4 carbon atoms or a hydrogen atom, respectively, $R^2$ represents any of an amino group, a hydrogen atom, a hydroxyl group and a lower alkoxy group having 1 to 4 carbon atoms, and p is an integer of 1 to 300.

6. The composition for cosmetics set forth in claim 1, wherein the composition is obtained by a process comprising:
   mixing the microparticulate titanium dioxide and the at least one of magnesium oxide, calcium oxide, magnesium hydroxide and calcium hydroxide;
   thereafter pulverizing or crushing the mixture with a jet air stream; and
   simultaneously adsorbing or bonding a lipophilizing agent onto the resultant pulverized or crushed mixture.

7. The composition for cosmetics set forth in claim 2, wherein the composition for cosmetics is obtained by a process comprising:
   mixing the microparticulate titanium dioxide and the at least one of magnesium oxide, calcium oxide, magnesium hydroxide and calcium hydroxide, and a clay mineral;
   thereafter pulverizing or crushing the mixture with a jet air stream; and
   simultaneously adsorbing or bonding a lipophilizing agent onto the resultant pulverized or crushed mixture.

8. A cosmetic formulated from the composition for cosmetics set forth in claim 1.

9. The cosmetic set forth in claim 8, wherein the composition for cosmetics constitutes 0.5 to 50 wt % of the total weight of the cosmetic.

10. The composition for cosmetics set forth in claim 1, wherein component (B) is at least one of magnesium oxide, calcium oxide and magnesium hydroxide.

11. The composition for cosmetics set forth in claim 2, wherein a weight ratio among (A) the microparticulate titanium dioxide; (B) the at least one of magnesium oxide, calcium oxide, magnesium hydroxide and calcium hydroxide; and (C) the clay mineral is 20-97 : 3-40 : up to 77.

12. The composition for cosmetics set forth in claim 2, wherein the composition for cosmetics is lipophilically treated with (D) a lipophilizing agent.

13. The composition for cosmetics set forth in claim 12, wherein the lipophilizing agent is at least one compound selected from the group consisting of an alkyl alkoxy silane represented by the following general formula (1), a reactive organosilicone represented by the following general formula (2), an acylated amino acid, a polyolefin, hydrogenated lecithin, dextrine fatty acid ester, a compound containing a perfluoroalkyl group or a perfluoropolyether group, and a saturated or unsaturated fatty acid having 12 to 22 carbon atoms (including one in the form of a salt);

$$(C_nH_{2n+1})_aSi(OC_mH_{2m+1})_b \quad (1)$$

wherein n is an integer of 1 to 18, m is an integer of 1 to 3, a and b represent an integer of 1 to 3, and a+b =4, $$(R^1{}_3SiO)(R^1{}_2SiO)_p(SiR^2{}_3) \quad (2)$$

wherein all of $R^1$ s are mutually independent, and represent a lower alkyl group having 1 to 4 carbon atoms or a hydrogen atom, respectively, $R^2$ represents any of an amino group, a hydrogen atom, a hydroxyl group and a lower alkoxy group having 1 to 4 carbon atoms, and p is an integer of 1 to 300.

14. The composition for cosmetics set forth in claim 12, wherein the lipophilizing agent is at least one of a compound selected from the group consisting of an alkyl alkoxy silane represented by the following general formula (1), a reactive organosilicone represented by the following general formula (2), an acylated amino acid (including one in the form of a salt), and a saturated or unsaturated fatty acid having 12 to 22 carbon atoms (including one in the form of a salt);

$$(C_nH_{2n+1})_aSi(OC_mH_{2m+1})_b \quad (1)$$

wherein n is an integer of 1 to 18, m is an integer of 1 to 3, a and b represent an integer of 1 to 3, and a+b=4, $$(R^1{}_3SiO)(R^1{}_2SiO)_p(SiR^2{}_3) \quad (2)$$

wherein all of $R^1$ s are mutually independent, and represent a lower alkyl group having 1 to 4 carbon atoms or a hydrogen atom, respectively, $R^2$ represents any of an amino group, a hydrogen atom, a hydroxyl group and a lower alkoxy group having 1 to 4 carbon atoms, and p is an integer of 1 to 300.

15. A cosmetic formulated from the composition for cosmetics set forth in claim 2.

16. The cosmetic set forth in claim 15, wherein the composition for cosmetics constitutes 0.5 to 50 wt % of the total weight of the cosmetic.

17. The composition for cosmetics set forth in claim 2, wherein component (B) is at least one of magnesium oxide, calcium oxide and magnesium hydroxide.

18. The composition for cosmetics set forth in claim. 1, wherein the primary particle diameter of the microparticulate titanium dioxide is from 10 to 120 nm.

* * * * *